United States Patent [19]

Cryz et al.

[11] Patent Number: 4,771,127
[45] Date of Patent: Sep. 13, 1988

[54] NONTOXIC PSEUDOMONAS AERUGINOSA POLYSACCHARIDE-TETANUS TOXOID AND POLYSACCHARIDE-TOXIN A CONJUGATE VACCINES

[75] Inventors: Stanley J. Cryz, Bolligen; Emil P. Furer, Muri, both of Switzerland

[73] Assignee: Swiss Serum & Vaccine Institute Berne, Berne, Switzerland

[21] Appl. No.: 892,846

[22] Filed: Aug. 4, 1986

[30] Foreign Application Priority Data

Sep. 27, 1985 [CH] Switzerland ............... 04199/85

[51] Int. Cl.$^4$ .................. C07K 17/00; A61K 39/104
[52] U.S. Cl. ................... 530/395; 530/402; 530/403; 530/405; 424/92; 514/54
[58] Field of Search .............. 424/92; 530/395, 402, 530/403, 405; 514/547; 536/55.1, 1.1

[56] References Cited

U.S. PATENT DOCUMENTS

| | | | |
|---|---|---|---|
| 4,356,170 | 10/1982 | Jennings et al. | 424/80 |
| 4,619,828 | 10/1986 | Gordon | 424/88 |
| 4,663,160 | 5/1987 | Tsay et al. | 424/92 |
| 4,693,891 | 9/1987 | Collins et al. | 424/92 |
| 4,707,543 | 11/1987 | Zollinger et al. | 530/350 |

OTHER PUBLICATIONS

Seid et al., *JBC* 1981, pp. 7305–7310.

*Primary Examiner*—John Kight
*Assistant Examiner*—Garnette D. Draper
*Attorney, Agent, or Firm*—Bradford E. Kile

[57] ABSTRACT

Polysaccharide-protein conjugates were synthesized utilizing polysaccharide derived from hydrolyized *Pseudomonas aeruginosa* lipopolysacharide covalently coupled to either tetanus toxoid or *P. aeruginosa* toxin A, utilizing a spacer molecule and a coupling agent. Conjugates produced in such a manner possess a molecular weight of greater than 350,000, are nontoxic and non-pyrogenic, and upon immunization of animals induced protective anti-LPS antibody and antibody which neutralizes the lethal effect of tetanus toxin or toxin A. The polysaccharide-tetanus toxoid conjugate and polysaccharide-toxin A conjugate are safe and immunogenic when parenterally administered to humans.

8 Claims, No Drawings

NONTOXIC PSEUDOMONAS AERUGINOSA POLYSACCHARIDE-TETANUS TOXOID AND POLYSACCHARIDE-TOXIN A CONJUGATE VACCINES

BACKGROUND OF THE INVENTION

*Pseudomonas aeruginosa* (*P. aeruginosa*) is a leading cause of life-threatening nosocomial infections, especially in a compromised host. Human immunity to *P. aeruginosa* has been correlated with humoral antibody to lipopolysaccharide (LPS) and toxin A, as described in Pollack M. Huang A. I., Prescott R. K., Young L. S., Hunter K. W., Cruess D. F., Tsai C. M., "Enhanced survival in *Pseudomonas aeruginosa* septicemia associated with high levels of circulating antibody to *Escherichia coli* endotoxin core," J. Clin., Invest. 1983; 72: 1874-1881; Pollack M., Young, L. S., "Protective activity of antibodies to exotoxin A and lipopolysaccharide at the onset of *Pseudomonas aeruginosa* septicemia in man," J. Clin. Invest. 1979; 63: 276-286; and Cross A. C., Sadoff J. C., Iglewski B. H., Sokol P. A., "Evidence for the role of toxin A in the pathogenesis of infection with *Pseudomonas aeruginosa* in humans," J. Infect. Dis. 1980; 142: 538-546.

Anti-LPS antibody has been shown to be highly protective against *P. aeruginosa* infections in a variety of animal model systems, as noted in Cryz S. J. Jr., Fürer E., Germanier R., "Protection against *Pseudomonas aeruginosa* infection in a murine burn wound sepsis model by passive transfer of antitoxin A, antilastase, and antilipopolysaccharide," Infect. Immun. 1983; 39: 1072-1079; Cryz S. J. Jr., Fürer E., Germanier R., "Passive protection against *Pseudomonas aeruginosa* infection in an experimental leukopenic mouse model," Infect. Immun. 1983; 40: 659-664; Kazmierowski J. A., Reynolds H. Y., Kauffmann J. C., Durbin W. A., Graw, R. G. Jr., Devlin H. B., "Experimental pneumonia due to *Pseudomonas aeruginosa* in leukopenic dogs: prolongation of survival by combined treatment with passive antibody to Pseudomonas and granulocyte transfusions," J. Infect. Dis. 1977; 135: 438-446; and Pier G. B., Sidberry H. F., Sadoff J. C., "Protective immunity induced in mice by immunization with high-molecular-weight polysaccharide from *Pseudomonas aeruginosa*," Infect. Immun. 1978; 22: 919-925. However, attempts to use native *P. aeruginosa* LPS as a vaccine have been hampered by a high frequency of adverse reactions following immunization and the need for numerous injections to evoke an optimal immune response, as noted in Alexander T. W., Fisher M., "Immunization against Pseudomonas infection after thermal injury," J. Infect. Dis. 1974; 130 (Suppl.): 152-158; Haghbin M., Armstrong D., Murphy M. L., "Controlled prospective trial of *Pseudomonas aeruginosa* vaccine in children with acute leukemia," Cancer 1973; 32: 761-766; and Young L. S., Meyer R. D., Armstrong D., "*Pseudomonas aeruginosa* vaccine in cancer patients," Annals Int. Med. 1973; 79: 518-527.

As described in Liu P.V., "Extracellular toxins of *P. aeruginosa*," J. Infect. Dis. 130 (Suppl.): 594-599 1974, toxin A is the most toxic product, on a weight basis, synthesized by *P. aeruginosa*. Toxin A acts to inhibit eucaryotic protein synthesis by catalyzing the transfer of the adenosine diphosphate-ribosyl (ADPR) moiety of nicotinamide adenine dinucleotide onto eucaryotic elongation factor 2, as discussed in Iglewski, B.H., Liu, P.V. and Kabat, D., "Mechanism of Action of *P. aeruginosa* exotoxin A: ADP-ribosylation of mammalian elongation factor 2 in vitro and in vivo," Infect. Immun. 15: 138-144, 1977 and Ohman, D.E., Burns R.P. and Iglewski B.H., "Corneal Infections in mice with toxin A and elastase mutants of *P. aeruginosa*," J. Infect. Dis. 142: 547-555, 1980. Antitoxin A antibody either passively administered or induced by active vaccination with a toxin A toxoid has provided significant protection against experimental *P. aeruginosa* infection. Additional investigations have demonstrated a direct correlation between antitoxic antibody and survival of patients from an episode of *P. aeruginosa* bacteremia, as described in Cross, A.S., Sadoff, J.C., Iglewski, B.H., and Sokol, P.A., "Evidence for the role of toxin A in the pathogenesis of human infection with Pseudomonas," J. Infect. Dis. 142: 538-46, 1980 and Pollack M.S. and Young, L.S., "Protective activity of antibodies to exotoxin A and lipopolysaccharides at the outset of *P. aeruginosa* septicemia in man," J. Clin. Invest. 63: 276-86, 1979.

Although native *P. aeruginosa* LPS contains protective serotype specific antigenic determinants, native LPS has been found to be too toxic for use in humans as a parenterally administered vaccine. Serotype specific antigenic determinants of *P. aeruginosa* are contained within the O-polysaccharide (PS) region of the LPS molecule, and although the PS can be isolated free of the toxic lipid A moiety of the LPS, the PS are non-immunogenic, as noted in Pier, G.B., Sidberry, H.F., and Sadoff, J.C., "Protective Immunity induced in mice by immunization with high molecular weight polysaccharide from *P. aeruginosa*," Infect. Immun. 22: 919-925, 1978 and Chester, I.R., Meadow, P.M., and Pitt, T.L., "The relationship between O-antigenic lipopolysaccharides and serological specificty in strains of *P. aeruginosa* of different O-serotypes," J. Gen. Microbiol, 78: 305-318, 1973. In order to induce a protective immune response to isolated PS, by the present invention isolated PS is covalently coupled to either tetanus toxoid or *P. aeruginosa* toxin A, which serve as "carrier proteins" for the PS. The conditions used to couple toxin A to PS effectively d-etoxify the toxin A molecule, thereby producing a PS-toxin A toxoid conjugate. The PS-toxin A and PS-tetanus toxoid conjugates are non-toxic, immunogenic and provide protection against experimental *P. aeruginosa* infections.

SUMMARY OF THE INVENTION

In one embodiment, the present invention comprises a method of producing an immunogenic *P. aeruginosa* polysaccharide-tetanus toxoid conjugate vaccine having the steps of: deriving polysaccharide from *P. aeruginosa* lipopolysaccharide; covalently linking a spacer molecule to the polysaccharide; contacting the polysaccharide-spacer molecule with tetanus toxoid and a water-soluble carbodiimide coupling compound; and recovering from the resultant mixture a polysaccharide-tetanus toxoid conjugate.

In another embodiment, the present invention comprises a method of producing a polysaccharide-toxin A conjugate having the steps of: deriving polysaccharide from *P. aeruginosa* lipopolysaccharide; oxidizing the polysaccharide; linking toxin A covalently to a spacer molecule using a water-soluble carbodiimide as a coupling agent; and contacting the toxin A-spacer molecule with oxidized polysaccharide to form an immunogenic polysaccharide-toxin A conjugate.

In another embodiment the present invention comprises an immunogenic P. aeruginosa vaccine comprised of a polysaccharide-tetanus toxoid conjugate.

In another embodiment the present invention comprises an immunogenic P. aeruginosa vaccine comprised of a polysaccharide-toxin A conjugate wherein the toxin A portion of the conjugate is detoxified by contact with the spacer molecule.

DETAILED DESCRIPTION OF THE INVENTION

In the description of the present invention hereinafter, reference is made to the following tables:

Table 1 presents the molecular weight, toxicity, pyrogenicity and immunogenicity of P. aeruginosa, strain PA220, polysaccharide derived from hydrolized LPS, tetanus toxoid, P. aeruginosa toxin A, polysaccharide-tetanus toxoid conjugate and polysaccharide-toxin A conjugate;

TABLE 1

Characteristics of PS, toxin A, tetanus toxoid, PS-toxin A and PS-tetanus toxoid conjugates

|  | PS | Tetanus Toxoid | Toxin A | PS-toxin A Conjugate | PS-tetanus Toxoid Conjugate |
|---|---|---|---|---|---|
| Molecular weight[1] | <70,000 | 150,000 | 66,000 | >350,000 | >350,000 |
| Toxicity[2] | Nontoxic | Nontoxic | 0.2 ug | Nontoxic | Nontoxic |
| Pyrogenicity[3] | 50 ug | 50 ug | ND[4] | 50 ug | 85 ug |
| Immunogenicity[5] | Non-immunogenic | Immunogenic (Anti-tetanus IgG) | Immunogenic (Antitoxin A IgG) | Immunogenic (Anti-PS and anti-toxin A IgG) | Immunogenic (Anti-PS and anti-tetanus toxin IgG) |

[1]Determined by gel filtration over a column of AcA34.
[2]Determined by intraperitoneal injection into 18–20 g female NMRI mice. Expressed as the mean lethal dose per mouse. Nontoxic signifies that a minimum of 50 ug of antigen administered intraperitoneally resulted in no mortality.
[3]The highest dose of antigen when administered to rabbits by the intravenous route which resulted in a rise in body temperature ≦ + 0.3° C. Expressed as ug/ml/kg body weight.
[4]ND = not determined.
[5]Determined by immunizing groups of 3 rabbits with 50 ug of each antigen per rabbit. Sera were analyzed for specific IgG antibody by ELISA.

Table 2 shows the protective capacity of P. aeruginosa PA220 LPS, the polysaccharide-tetanus toxoid conjugate and the polysaccharide-toxin A conjugate vaccine against fatal P. aeruginosa burn wound sepsis in mice;

TABLE 2

Protection against fatal P. aeruginosa PA220 burn wound sepsis by immunization with PA220 LPS, PS-tetanus toxoid conjugate and PS-toxin A conjugate

| Immunogen[1] | LD$_{50}$[2] |
|---|---|
| None | 20 |
| LPS | 10$^6$ |
| PS-tetanus toxoid conjugate | 10$^6$ |
| PS-toxin A conjugate | 10$^6$ |

[1]Mice each received 1 ug of antigen intramuscularly on days 0 and 14 and were challenged subsequent to burn trauma on day 28 with graded doses of P. aeruginosa PA220 in accord with the method described in Holder, I. A.; Wheeler, R., and Mortie, T. C., "Flageller preparations from P. aeruginosa: animal protection studies," Infect. Immun. 35: 276–80, 1982.
[2]LD$_{50}$ = mean lethal dose. Calculated by the method described in Reed R. J. and Muench H. A., "Simple method of estimating 50 percent end points," Am. J. Hyg. 27: 493–97, 1938.

Table 3 presents reactions noted by human volunteers after parenteral immunization with 100 ug of polysaccharide-tetanus toxoid conjugate;

TABLE 3

Reactions following vaccination with PS-tetanus toxoid vaccine

| Immunization | Local Reactions | | | | Systemic Reactions | | | | |
|---|---|---|---|---|---|---|---|---|---|
|  | Pain | Swelling | Redness | Total[1] | Fever | Malaise | Headache | Other[2] | Total[1] |
| 1 | 6 | 2 | 1 | 6/16 | 0 | 1 | 0 | 1 | 2/16 |
| 2 | 3 | 2 | 2 | 6/15[3] | 0 | 0 | 0 | 0 | 0/15 |

[1]Number of volunteers noting a reaction/total number of volunteers.
[2]One vaccine experienced swollen lymph nodes at 48 h post-vaccination.
[3]One subject did not receive a second dose of vaccine.

Table 4 shows the anti-PA220 LPS immunoglobulin G response in volunteers after immunization with the polysaccharide-tetanus toxoid vaccine; and

TABLE 4

Anti-PA220 LPS IgG antibody response following immunization with PS-tetanus toxoid conjugate

| Mean ELISA titer (range)[1] | | | Nr. ≧ 4-fold increase in titer (%)[4] |
|---|---|---|---|
| Pre-immune[2] | Post-immune[3] | | |
|  | 14 days | 28 days |  |
| 43 (14–128) | 652 (39–3,200)[5] | 823 (47–4,400)[5] | 13/16 (82) |

[1]ELISA titers determined as described in Cryz, S. J. Jr., E. Furer, and R. Germanier, "Protection against P. aeruginosa infection in a murine burn wound sepsis model by passive transfer of antitoxin A, antielastase, and anti-lipopolysaccharide", Infect. Immun. 1983; 39: 1072–1079.
[2]Pre-immune = at time of immunization.
[3]Post-immune = days post-immunization.
[4]Determined by dividing post-immune titer by pre-immune titer.
[5]The mean post-immune titer was significantly elevated (p < 0.01 as determined by students t-test) as compared to pre-immune titer.

Table 5 shows the ability of human immunoglobulin G antibody elicited in response to vaccination with the polysaccharide-tetanus toxoid conjugate to protect mice against fatal P. aeruginosa sepsis.

TABLE 5

Capacity of passively transferred human IgG to prevent fatal *P. aeruginosa* PA220 burn wound sepsis in mice

| IgG Transferred[1] | Anti-LPS IgG ELISA titer | $LD_{50}$ |
|---|---|---|
| None[2] | — | $<1.3 \times 10^1$ |
| Pre-immune[3] | 73 | $1.3 \times 10^{3(5)}$ |
| Post-immune[4] | 1065 | $6.7 \times 10^{5(6)}$ |

[1]Mice received approximately 160 ug of human IgG intravenously in 0.2 ml 24 hours prior to challenge with *P. aeruginosa* PA220.
[2]Mice received 0.2 ml of sterile saline.
[3]Prepared from equal aliquots of serum taken from all volunteers prior to immunization.
[4]Prepared from equal aliquots of serum taken from all volunteers 28 days post-immunization.
[5]95% confidence interval compared to $LD_{50}$ of mice which received no IgG.
[6]95% confidence interval compared to $LD_{50}$ of mice which received no IgG or pre-immune IgG.

Table 6 shows the composition of conjugates formed by covalently coupling polysaccharides derived from various serotypes of LPS to tetanus toxoid.

TABLE 6

Composition of polysaccharide-tetanus toxoid conjugates

| Serotype of polysaccharide (IATS) | Conjugate composition (%) | |
|---|---|---|
| | polysaccharide[1] | tetanus toxoid[2] |
| 1 | 27 | 73 |
| 2 | 17 | 83 |
| 3 | 22 | 78 |
| 4 | 22 | 78 |
| 6 | 43 | 57 |
| 7 | 39 | 61 |
| 10 | 40 | 60 |
| 11 | 21.5 | 78.5 |
| 16 | 32 | 68 |

[1]Quantitated by the phenol-sulfuric acid method of Dubois et al.
[2]Quantitated by the method of Lowry et al.

Table 7 shows the composition, molecular weight, ADPR-transferase ctivity and pyrogenicity of a PS-toxin A conjugate vaccine administered to human volunteers:

TABLE 7

Characteristics of PS-toxin A conjugate vaccine

| Composition (%)* | | $M_r^+$ | ADPR-transferase activity | Pyrogenicity** ($\mu g/kg$) |
|---|---|---|---|---|
| protein | carbohydrate | | | |
| 70.2 | 29.8 | >350,000 ($2 \times 10^6$) | ND*** | 50 $\mu g$ |

*Values shown are on a weight basis.
+Determined by filtration over Sephacryl S-500.
**ND = none-detected.
***When administered intravenously to rabbits, 50 $\mu g$ of vaccine per kg body weight evoked <0.5° C. increase in temperature.

Table 8 presents reactions noted by human volunteers following immunization with PS-toxin A conjugate:

TABLE 8

Reactions noted following immunization with PS-toxin A conjugate

| Immunization | Local reactions | | | Systemic reactions | | | |
|---|---|---|---|---|---|---|---|
| | pain | swelling | redness | itching | fever | chills | malaise | headache |
| 1 | 1 | 0 | 0 | 0 | 0 | 0 | 1 | 0 |
| 2 | 4 | 2 | 1 | 1 | 0 | 0 | 2 | 2 |

Table 9 shows the immune response of human volunteers to vaccination with PS-toxin A conjugate:

TABLE 9

Immune response to vaccination with PS-toxin A conjugate vaccine

| Immunizing dose* | Immune response to | Mean $\mu g$ IgG/ml (Nr. ≧ fold rise/total)+ Day** | | | Peak fold rise |
|---|---|---|---|---|---|
| | | 0 | 14 | 42 | |
| 81.25 | toxin A | 0.61 | 19.9 (4/10) | 22.5 (6/10) | 37 |
| | LPS | 9.3 | 108.7 (7/10) | 63.3 (7/10) | 11.6 |
| 162.5 | toxin A | 3.2 | 45.5 (4/10) | 69.7 (9/10) | 21.5 |
| | LPS | 3.8 | 73.8 (7/10) | 81 (9/10) | 21.3 |

*Volunteers were immunized on day 0 and day 28. Subjects vaccinated with 81.25 $\mu g$ of conjugate received 25 $\mu g$ of O-PS and 56.25 $\mu g$ of toxin A protein. Subjects vaccinated with 162.5 $\mu g$ of conjugate received 50 $\mu g$ of O-PS and 112.5 $\mu g$ of toxin A protein.
+Indicates number of volunteers presenting with a 4-fold or greater rise in specific IgG compared to preimmunization levels.
**Relative to the time of immunization (day 0).

Table 10 shows the ability of human antitoxin IgG elicited in response to vaccination with PS-toxin A conjugate to neutralize the toxic effect of toxin A:

TABLE 10

Ability of PS-toxin A conjugate vaccine to elicit toxin A-neutralizing antibody

| Immunizing dose* ($\mu g$ PS) | | Mean $\mu g$ toxin A neutralized per ml of serum (range) |
|---|---|---|
| 81.25 | pre-immune+ | <0.312 |
| | post-immune** | 3.1 (<0.312–19.9) |
| | mean-fold rise*** | 9.8 |
| | nr. ≧ 2-fold rise | 5/10 |
| | nr. ≧ 4-fold rise | 3/10 |
| 162.5 | pre-immune+ | <0.312 |
| | post-immune** | 2.9 (<0.312–1.248) |
| | mean-fold rise*** | 9.2 |
| | nr. ≧ 2-fold rise | 9/10 |
| | nr. ≧ 4-fold rise | 6/10 |

*Volunteers immunized with 81.25 $\mu g$ of conjugate received 25 $\mu g$ of O-PS and 56.25 $\mu g$ of toxin A protein. Volunteers immunized with 162.5 $\mu g$ of conjugate received 50 $\mu g$ of O-PS and 112.5 $\mu g$ of toxin A protein.
+At time of immunization.
**For serum collected at day 42.
***Mean post-immune neutralizing capacity divided by mean pre-immune neutralizing capacity.

Table 11 presents the composition of conjugates formed by covalently coupling polysaccharide derived from various serotypes of LPS to toxin A:

TABLE 11

Composition of polysaccharide-toxin A conjugates

| Serotype of polysaccharide (IATS) | Conjugate composition (%) | |
|---|---|---|
| | polysaccharide[1] | toxin $A^2$ |
| 1 | 35.5 | 64.5 |
| 2 | 35.5 | 64.5 |
| 3 | 27.5 | 72.5 |
| 4 | 28.6 | 71.4 |
| 6 | 43 | 57 |
| 7 | 26.5 | 73.5 |
| 10 | 35.5 | 64.5 |
| 11 | 35.5 | 64.5 |
| 16 | 29.6 | 70.4 |

[1]Quantitated by the phenol-sulfuric acid method of Dubois et al.
[2]Quantitated by the method of Lowry et al.

In generating the data included herein *P. aeruginosa* strain PA220, Habs serotype 6, supplied by Dr. B. Wretlind, Karolinska Institute, Stockholm, Sweden, was used as the source of lipopolysaccharide (LSP). It is to be understood other strains of *P. aeruginosa* could be used as a source of LPS, such as presented in the following table, though not necessarily with equivalent results:

| Strain Designation | International Antigen Typing System (IATS) Serotype | Source |
|---|---|---|
| PA53 | 1 | Walter Reed Army Institute of Research, Washington, D.C. |
| E576 | 2 | Walter Reed Army Institute of Research, Washington, D.C. |
| 8505 | 3 | Public Health Laboratory Service, Colindale, London, England |
| 6511 | 4 | Public Health Laboratory Service, Colindale, London, England |
| ATCC 27318 | 16 | M. Fisher Parke Davis and Co., Detroit, Michigan |
| ATCC 27317 | 7 | M. Fisher Parke Davis and Co., Detroit, Michigan |
| ATCC 27316 | 10 | M. Fisher Parke Davis and Co., Detroit, Michigan |
| ATCC 27313 | 11 | M. Fisher Parke Davis and Co., Detroit, Michigan |

The strain PA220 was serotyped as immunotype 1 according to the Fisher-Devlin Typing System described in Fisher M., Devlin, H. B., Gnabsik, F., "New immunotype schema for *P. aeruginosa* based on protective antigen," S. J. Bacterial 1969; 98: 835-36 or type 6 by the International Antigenic Typing System (Difco Laboratories, Detroit, Mich.). Cultures for challenge experiments were grown as previously described in Cryz, S.J., Furer, E., Germanier, R., "Protection against *P. aeruginosa* infection in murine burn wound sepsis model by passive transfer of antitoxin A, antielastase and antilipopolysaccharide," Infect. Immun. 1983, 39: 1072-79.

Nontoxic immunogenic conjugates were synthesized by covalently linking polysaccharide containing serological determinants derived from hydrolized *Pseudomonas aeruginosa* PA220 LPS to tetanus toxoid and polysaccharide derived from *P. aeruginosa* ATCC 27317 in an identical manner to *P. aeruginosa* toxin A. Adipic acid dihydrazide was used as a spacer molecule. The coupling of toxin A to polysaccharide in this manner results in the detoxification of toxin A, in essence producing a toxin A toxoid. The conjugates produced in this manner possess a molecular weight of greater than 350,000, are nontoxic and nonpyrogenic, and induce antibody to both-the polysaccharide and protein carrier, which when administered to animals are protective against experimental *P. aeruginosa* infections.

The polysaccharide-tetanus toxoid conjugate is safe when parenterally administered to human volunteers. Vaccination engendered an anti-polysaccharide and an anti-tetanus toxin antibody response. These antibodies were protective against fatal *P. aeruginosa* infections when passively transferred to mice and neutralized the toxic effect of tetanus toxin.

By the method of the present invention, LPS was isolated and purified as described by S. J. Cryz, E. Furer and R. Germanier (1984), "Protection against fatal *P. aeruginosa* burn wound sepsis by immunization with lipopolysaccharide and high molecular weight polysaccharide," Infect. Immun. 43: 795-799. LPS prepared in this manner contained less than 1% (wt/wt) protein and less than 1% (wt/wt) nucleic acids. Polysaccharide (PS) containing serospecific antigenic determinants was derived from LPS by mild acid hydrolysis. The PS was derived from LPS by placing the LPS in 1% (vol/vol) acetic acid and heating for 1.5 hours at 100° C., as described by D. T. Drewry, K. C. Symes, G. W. Gray and S. G. Wilkinson (1975), "Studies in polysaccharide fractions from the lipopolysaccharide of *P. aeruginosa*," Biochem J. 149: 93-106. Although, as noted above, in the preparation described herein PS was derived from LPS by treatment with acetic acid for 1.5 hours at 100° C., it is to be understood that other conditions for deriving PS from LPS are within the scope of the present invention, such as treatment with acetic acid for between ½ hour to 48 hours and in a temperature range of from 70° C. to 100° C. The major portion of the toxic lipid A moiety which was cleaved from PS by this procedure was removed by centrifugation. The supernatant was retained and extracted three times with a solution of chloroform:methanol (3:1) to remove residual lipid A. The aqueous PS-containing phase was retained and concentrated by rotary evaporation over reduced pressure. This material was chromatographed over a column of AcA34 (LBK-Produkter, Bromma, Sweden). Polysaccharide with a molecular weight of approximately 10,000–75,000 was in this way collected, and lyophilized.

PS was next oxidized to generate reactive aldehyde groups as follows. PS was dissolved in distilled water to a final concentration of 5 mg/ml. $NaIO_4$ was then added to yield a final concentration of 0.1 M. This mixture was then stirred for 2 hours at 22° C. protected from light. At this time 0.53 ml of ethyleneglycol for the purpose of reacting with residual $NaIO_4$ was added and stirring continued for 30 minutes at 22° C. This material was then extensively dialyzed against distilled water and in turn, lyophilized.

Toxin A was purified as described in the Cryz, Furer, Germanier reference "Protection against fatal *P. aeruginosa* infection in a murine burn wound sepsis model by passive transfer of antitoxin A, antielastase and antilipopolysaccharide," noted above, except that the production strain was a spontaneously isolated hyperproducer of toxin A derived from *P. aeruginosa* strain PA103 (supplied by Dr. B. Wretlind, Karolinska Institute, Stockholm, Sweden) termed PA103-FeR. The final preparation consisted of greater than 95% toxin A protein as determined by high pressure liquid chromatography.

Adipic acid dihydrazide (ADH) was utilized as a spacer molecular to facilitate the covalent linking of toxin A to oxidized PS. ADH was linked to toxin A as follows. Toxin A was diluted to 5 mg/ml in 0.05 M $NaPO_4$, pH 7.2. ADH (Fluka A. G., Buchs, Switzerland) and 1-ethyl-3 (-3-dimethylaminopropyl) carbodiimide were each added as a solid to yield a final concentration of 10 mg/ml of each reagent. This mixture was in turn dialyzed against 0.05 M $NaPO_4$, pH 8 buffer, for a period of 72 hours at 4° C. This mixture was subsequently dialyzed against 0.5 M $NaPO_4$, pH 8 buffer, for a period of 4 hours at 22° C. The resulting insoluble material was removed by centrifugation and the toxin A product concentration adjusted to 5 mg/ml. This product is termed toxin A-ADH.

Toxin A-ADH was covalently coupled to the oxidized PS in the following manner. Toxin A-ADH (in 0.5 M NaP04, pH 8 buffer) was adjusted to a concentration of 5 mg/ml and added to an equal amount of oxidized PS (5 mg/ml). The components were mixed by stirring for 6 hours at 22° C. At this time 3.1 ml of 0.25 M NaCNBH3 was added, followed by stirring for 5 days at 22° C. This mixture was then dialyzed for a period of 24 hours against phosphate buffer saline, pH 7.4, containing 0.02% merthiolate. Insoluble material was removed by centrifugation and the mixture chromatographed over a column of AcA34 (LKB-Produkter, Bromma, Sweden). Fractions were collected and monitored for absorbance at 220 nm and 280 nm. The material which eluted in the void (Vo), possessing a molecular weight of greater than 350,000 (which exceeded that of the starting PS or toxin A-ADH) representing the PS-toxin A conjugate, was collected and lyophilized. The conjugate was composed of 27.5% PS of the same serotype as determined by the phenol sulfuric acid method described by Dubois et al. [M. Dubois, K. A. Giles, J. K. Hamilton, P. A. Rebers, and F. Smith (1956) Anal. Chem. 28, 350–356] using PS as a standard, and 72.5% toxin A as determined by the procedure of Lowry et al. [O. H. Lowry, N. J. Rosenbrough, A. L. Farr and R. J. Randall (1951) J. Biol. Chem. 193, 265–275] using bovine serum albumin as a standard. It is to be understood that NaCNBH3 was utilized in the above procedure for the purpose of reducing Schiff's bases formed above, and other compounds exhibiting similar properties, such as NaBH4 could be used.

In accordance with the present invention, the synthesis of the PS-tetanus toxoid conjugate procedes as follows.

Tetanus toxoid for human use (TE Anatoxine, Swiss Serum and Vaccine Institute, Berne, Switzerland) was used as a starting material. Tetanus toxoid contained in TE Anatoxine was purified by ion-exchange chromatography on DEAE-cellulose (Pharmacia Fine Chemicals, Uppsala, Sweden) followed by gel filtration over AcA44 (LBK-Produkter, Bromma, Sweden). The final preparation consisted of greater than 90% tetanus toxoid.

PS was isolated from LPS by acid hydrolysis as described above. However, PS was employed in the non-oxidized form in the conjugation with tetanus toxoid. PS (100 mg) was dissolved in 9.2 ml distilled water. Cyanogen bromide (0.44 ml of a 160 mg/ml solution) was added for the purpose of introducing reactive cyclic immidocarbonate or cyanate ester groups into the polysaccharide and the pH maintained for six minutes at 10.5 by the addition of 0.1 N NaOH. The pH was then lowered to 8.6 by the addition of solid NaHCO3 and 0.4 g of ADH was added to equal 5 mg/ml. This mixture was stirred for 16 hours at 4° C., followed by dialysis for a period of 72 hours against water. The pH of the solution was lowered to 4.8 by the addition of HCl. Tetanus toxoid (100 mg) and 1-ethyl 3- (-3-dimethylaminopropyl carbodiimide (400 mg) were added and the mixture stirred for 4 hours at 22° C. Following extensive dialysis for a period of 48 hours against phosphate buffered saline, pH 7.4, the mixture was chromatographed over a column of AcA34. Fractions were collected and monitored for total protein content and total carbohydrate content. The material which eluted in the void column, (Vo) possessing a molecular weight in excess of 350,000, which exceeds that of the starting PS or tetanus toxoid representing the PS-tetanus toxoid conjugate, was collected and lyophilized. The conjugate was composed of 47.3% tetanus toxoid (as determined by the method of Lowry et al. using bovine serum albumin as a standard) and 52.7% PS (as determined by the phenol sulfuric acid method using PS as a standard).

In the preparation of the polysaccharide-tetanus toxoid conjugate and the polysaccharide-toxin A conjugate described above, adipic acid dihydrazide was utilized as a spacer molecule. If desired, other spacer molecules such as dicarboxylic acid dihydrazides of the following nature NH2—NH—CO—(CH2)$_n$—CONHNH2, where n=1–10, could be utilized in the preparation of these conjugates though not necessarily with equivalent results.

Characteristics of PS-toxin A and PS-tetanus toxoid conjugates

Immunogenic characteristics of the PS-toxin A and PS-tetanus toxoid conjugates are shown in Tables 1 through 11. With specific regard to Table 1, the conjugate vaccines both possessed a molecular weight in excess of 350,000, which exceeded the molecular weight of their respective starting constituents (i.e., PS and either tetanus toxoid or toxin A). Toxin A was highly lethal for mice with a mean lethal dose of 0.2 ug/mouse. However, covalent coupling of toxin A to PS resulted in a marked reduction in toxicity. There was no mortality among mice which received 200 ug of toxin A protein conjugated to PS intraperitoneally. Thus, the method described herein utilized to produce the PS-toxin A conjugate reduces its toxicity by a minimum of 1000-fold, in effect resulting in a toxin A toxoid. All antigens, with the exception of toxin A which was not assayed for pyrogenicity due to its highly toxic nature, were nonpyrogenic when intravenously administered to rabbits in contrast to native P. aeruginosa PA220 LPS which was pyrogenic at a dose of 0.7 ug/ml/kg body weight). PS alone was found to be non-immunogenic in rabbits. In contrast, the PS-tetanus toxoid conjugate and the PS-toxin A conjugate were found to induce antibody to both the PS and respective carrier protein moieties.

Summarizing the data shown in Table 1: the PS-toxin A conjugate and the PS-tetanus toxoid conjugate were of a high molecular weight, nontoxic, nonpyrogenic and induced a specific antibody response to both the PS and carrier protein moiety. Furthermore, the conjugation conditions utilized produced a safe and immunogenic toxin A toxoid.

The ability of the PS-toxin A conjugate vaccine to prevent fatal intoxication of mice challenged with purified toxin A was determined in the following manner. Groups of mice received either 10 ug of PS-toxin A conjugate or buffer (control groups) intramuscularly on days 0 and 14. Mice were challenged intraperitoneally on day 28 with grade doses of toxin A. The mean lethal dose for the control group was 0.2 ug/mouse, whereas that for the immunized group 4.7 ug/mouse, demonstrating that immunization with the PS-toxin A conjugate induces antibody capable of neutralizing the in vivo toxicity of toxin A.

The ability of native LPS, the PS-tetanus toxoid conjugate and the PS-toxin A conjugate to protect against experimental P. aeruginosa burn wound sepsis is shown in Table 2. Immunization with LPS, PS-tetanus toxoid conjugate or PS-toxin A conjugate were equally effective at preventing fatal sepsis, increasing the mean lethal dose for P. aeruginosa PA220 50,000-fold over that for the unimmunized group.

Safety and Immunogenicity of PS-tetanus toxoid vaccine in humans

The PS-tetanus toxoid vaccine was prepared as follows. PS-tetanus toxoid conjugate in phosphate-buffered saline plus 5% (wt/vol) lactose was passed through a filter (0.45 um pore size) and aseptically aliquoted into vials (1 human dose per vial =100 ug of conjugate). The material was lyophilized and sealed under aseptic conditions.

Tests for sterility and general safety of the vaccine was performed according to the procedure detailed under articles V.2.1.1 and V.2.1.5 of the European Pharmacopoeia, 2d ed., Sainte Ruffine, France: Maisonneuve, S.A. The conjugate utilized in this example was composed of 47.3% protein and 52.7% carbohydrate and bound both anti-PA220 LPS IgG and anti-tetanus toxoid IgG when used as an immobilized antigen in an ELISA assay system. The vaccine was found to be comparatively non-pyrogenic for rabbits. The minimal pyrogenic dose for PA220 LPS was 0.7 ug/kg whereas that for the vaccine was more than 100-fold higher (85/ug). The vaccine was nontoxic for mice and guinea pigs when injected intraperitoneally (100 ug/animal) as evidenced by no overt signs of illness and normal weight gain curves. When analyzed by gel immunodiffusion, the conjugate gave a line of identity with PA220 LPS and tetanus toxoid when tested against anti-PA220 LPS or anti-tetanus toxoid.

Healthy adult volunteers aged 16-59 years of both sexes received 100 ug of conjugate in 0.5 ml pyrogen free water subcutaneously in the deltoid area on days 0 and 14. All reactions were recorded by the volunteers on a control sheet for 5 days post-vaccination. Venous blood samples were drawn at the time of vaccination and at 14 days and 28 days post-vaccination. The sera was collected and stored at $-20°$ C. Immunoglobulin G (IgG) antibody titers were determined by ELISA assay as previously described in S. J. Cryz, Jr., E. Furer, and R. Germanier (1983), Infect. Immun. 39: 1072-1079.

Reactions to vaccination are detailed in Table 3. Approximately 40% of the vaccinees noted a local reaction following either immunization. In most instances symptoms persisted for 24 hours or less. Only two systemic reactions were noted, both after primary vaccination. One vaccinee experienced malaise 4 hours post-immunization which lasted for 4 hours. A second subject reported swollen regional lymph nodes draining the site of inoculation. All symptoms were spontaneously resolved and did not interfere with normal activities.

Immunization with the PS-tetanus toxoid conjugate resulted in a significant ($p<0.01$) rise in the mean anti-PA220 LPS IgG titer at 14 days and 28 days post-vaccination as compared to the mean pre-immune titer. (Table 4). Over 80% (13/16) of the volunteers responded with a significant (4-fold or greater) increase in anti-PA220 LPS IgG titer. Immunization with the conjugate also resulted in an increase in tetanus toxin neutralizing antibody titer. Two serum pools were made by combining an equivalent amount of serum from each individual at the time of immunization (pre-immune pool) and 28 days post-immunization (immune pool). The pre-immune pool possessed 2.7 international tetanus toxoid neutralizing units per ml of serum, whereas the immune pool possessed 6.2 units per ml of serum.

Anti-PA220 LPS IgG antibody evoked by vaccination of humans with the PS-tetanus toxoid conjugate vaccine was found to be highly effective at preventing fatal experimental *P. aeruginosa* sepsis (Table 5). Passively transferred post-immune IgG was significantly ($p<0.05$) more effective at preventing death than passively transferred pre-immune IgG. Protection correlated with the anti-PA220 LPS IgG titers possessed by the IgG preparations.

To summarize the data from Tables 3-5: the PS-tetanus toxoid conjugate was found to be safe when parenterally administered to humans, evoking only mild, self-limiting reactions in less than half the subjects. The conjugates elicited a significant increase in anti-PA220 LPS IgG titers in greater than 80% of vaccinees. This anti-PA220 LPS IgG was found to be highly protective against fatal experimental *P. aeruginosa* PA220 sepsis.

Safety and Immunogencity of PS-toxin A conjugate in humans

As noted previously, Table 7 presents various characteristics of the PS-toxin A conjugate administered to human volunteers. The conjugate was composed of 70.2% toxin A (protein) and 29.8% carbohydrate (PS). The molecular weight of the conjugate was approximately $2 \times 10^6$ It was devoid of ADPR-transferase activity and was nonpyrogenic. It is important to note that the toxic nature of toxin A is believed to be due to its ADPR-transferase activity, and the fact that the conjugate lacks this activity explains its nontoxic nature. As shown in the table below, toxin A is rendered non-toxic through the covalent linkage of toxin A with the ADH spacer molecule.

| Toxicity of toxin A and toxin A-ADH | |
|---|---|
| Antigen | Mean lethal dose[1] |
| toxin A | 0.2 ug |
| toxin A-ADH | >10 ug[2] |

[1]Expressed as ug of antigen per mouse administered intraperitoneally.
[2]More than 50% of the animals survived.

Twenty healthy adult volunteers were vaccinated with the polysaccharide-toxin A conjugate vaccine. As shown in Table 8, reactions to immunization were mild in nature, consisting primarily of local discomfort at the injection site. All symptoms were spontaneously resolved of their own accord and did not hinder the normal activity of the vaccinees.

The immune response of the volunteers to vaccination is shown in Table 9. The conjugate, at both doses tested, was capable of eliciting immunoglobulin G (IgG) antibody to both the PS component (represented by anti-LPS IgG) and the toxin A component (represented by antitoxic IgG). Peak fold rises in IgG to toxin A were from 21.5-fold to 37-fold (for the 162.5 ug dose and the 81.25 ug dose, respectively). The mean fold rise in IgG to LPS ranged from 11.6-fold to 21.3-fold (for the 81.25 ug dose and the 162.5 ug dose, respectively). At 42 days post-immunization, the seroconversion rate ($\geq$4-fold rise) ranged from 60% to 90% for both toxin A and LPS at the 162.5 ug dose.

As presented in Table 10, antitoxin IgG elicited in response to vaccination with the PS-toxin A conjugate was found to be capable of neutralizing the toxin effect of toxin A.

In addition, as shown in Tables 6 and 11, the procedure described therein can be utilized to synthesize conjugates composed of various serotypes of PS using either toxin A or tetanus toxoid as a carrier protein.

These conjugates of different polysaccharide serotypes can be combined to form polyvalent polysaccharide-tetanus toxoid and polysaccharide-toxin A vaccines of various polysaccharide serotype combinations.

PS-tetanus toxoid conjugate and PS-toxin A conjugation in vaccine use

The usefulness of PS-tetanus toxoid conjugate and PS-toxin A conjugate as a vaccine is apparent from the data presented in Tables 1–11. Both conjugates are nontoxic and nonpyrogenic. Immunization with either conjugate evokes serotype-specific anti-LPS antibody which is highly protective against experimental *P. aeruginosa* burn wound sepsis. The PS-toxin A conjugate described herein also engenders a toxin A neutralizing antibody response in addition to eliciting protective anti-LPS IgG antibody, and the protective capacity of specific antitoxin A antibody has been demonstrated. As described previously, passive transfer of an antitoxin A globulin protected mice against lethal intraperitoneal infections with *P. aeruginosa*, and passively administered antitoxin A antibody protected mice which were burn-traumatized from subsequent *P. aeruginosa* infections. In addition, the ability of the PS-toxin A conjugate to evoke an immunogenic response to humans to both LPS and toxin A has been demonstrated.

In humans, a *P. aeruginosa* bacteremic episode has been shown to result in an increase in serum antitoxin A titers. High titers of antitoxin A antibody at the onset of *P. aeruginosa* bacteremia correlate with an increased survival rate and it has been shown that those patients who survived a bacteremic infection with a toxin-A producing strain of *P. aeruginosa* had sub stantially higher mean peak antitoxin A titers (25.8±5.5 ug/ml) than patients who died from such infections (4.6±2.0 ug/ml) as described in A. S. Cross, J. C. Sadoff, B. H. Iglewski, and P. A. Sokol (1980), J. Infect. Dis. 142: 538–546. The mechanisms by which anti-LPS and antitoxin A mediate their protective capacity based upon survival rates for humans suffering from *P. aeruginosa* bacteremia appear to be different and synergistic. Therefore, since the PS-toxin A conjugate elicits 2 types of protective antibodies, anti-LPS and antitoxin A, this conjugate provides a higher degree of protection against *P. aeruginosa* infection than a corresponding vaccine which would induce only anti-LPS antibody.

While a preferred embodiment of the invention has been described herein, it will be obvious to those skilled in the art that various changes and modifications may be made without departing from the spirit of the invention as defined in the following claims.

We claim:

1. An immunogenic conjugate, comprising (i) a *P. aeruginosa* polysaccharide covalently linked through at least one of a hydroxyl or carboxyl group of said polysaccharide, said polysaccharide being essentially free of lipid A, to (ii) a tetanus toxoid carrier protein.

2. An immunogenic conjugate, comprising (i) a *P. aeruginosa* polysaccharide covalently linked through at least one of a hydroxyl or carboxyl group of said polysaccharide, said polysaccharide being essentially free of lipid A, to (ii) a toxin A carrier protein.

3. The conjugate according to claim 1 or 2 wherein said conjugate has a molecular weight greater than 350,000.

4. The immunogenic conjugate according to claim 1 or 2 further comprising a spacer molecule, wherein said polysaccharide is covalently linked to said carrier protein through said spacer molecule.

5. The immunogenic conjugate according to claim 4 wherein said spacer molecule is water soluble adipic acid dihydrazide.

6. A *P. aeruginosa* immunogenic vaccine comprising said conjugate according to claim 1 or 2 and a pharmaceutically acceptable carrier, wherein said conjugate is present in an amount sufficient to elicit an immunogenic effect.

7. The vaccine according to claim 6 wherein said vaccine is nontoxic and nonpyrogenic.

8. The vaccine according to claim 6 wherein said vaccine is capable of inducing antibodies to both said polysaccharide and said carrier protein of said conjugate.

* * * * *